United States Patent
Geng et al.

(10) Patent No.: US 9,896,423 B2
(45) Date of Patent: Feb. 20, 2018

(54) DEUTERIUM SUBSTITUTED 1-[2-(2,4-DIMETHYL-PHENYLSULFANYL)-PHENYL]PIPERAZINE COMPOUND OR DERIVATIVES THEREOF, AND PHARMACEUTICAL COMPOSITION AND USE THEREOF

(71) Applicants: Jiangsu Jibeier Pharmaceutical Co. Ltd., Jiangsu (CN); Zhenjiang San An Pharmaceutical Co. Ltd., Jiangsu (CN)

(72) Inventors: Zhongyi Geng, Jiangsu (CN); Xinghai Chen, Jiangsu (CN); Parker Aulma, Jiangsu (CN); Wei Peng, Jiangsu (CN)

(73) Assignees: Jiangsu Jibeier Pharmaceutical Co., Ltd., Jiangsu (CN); Zhenjiang San An Pharmaceutical Co., Ltd., Jiangsu (CN)

( * ) Notice: Subject to any disclaimer, the term of this patent is extended or adjusted under 35 U.S.C. 154(b) by 0 days.

(21) Appl. No.: 15/315,182

(22) PCT Filed: Sep. 28, 2014

(86) PCT No.: PCT/CN2014/087662
§ 371 (c)(1),
(2) Date: Nov. 30, 2016

(87) PCT Pub. No.: WO2015/180342
PCT Pub. Date: Dec. 3, 2015

(65) Prior Publication Data
US 2017/0197927 A1  Jul. 13, 2017

(30) Foreign Application Priority Data
May 30, 2014  (CN) .......................... 2014 1 0244856

(51) Int. Cl.
*C07D 295/096* (2006.01)
*C07B 59/00* (2006.01)

(52) U.S. Cl.
CPC ........ *C07D 295/096* (2013.01); *C07B 59/002* (2013.01); *C07B 2200/05* (2013.01)

(58) Field of Classification Search
None
See application file for complete search history.

(56) References Cited

U.S. PATENT DOCUMENTS

| | | | | |
|---|---|---|---|---|
| 6,603,008 | B1 * | 8/2003 | Ando | C07D 405/14 546/269.7 |
| 7,138,407 | B2 * | 11/2006 | Ruhland | C07D 211/20 514/212.01 |
| 2007/0155820 | A1 | 7/2007 | Gant et al. | |
| 2010/0297240 | A1 | 11/2010 | Bang-Andersen et al. | |
| 2012/0302553 | A1 | 11/2012 | Ruhland et al. | |
| 2014/0163043 | A1 | 6/2014 | Ruhland et al. | |
| 2015/0196544 | A1 | 7/2015 | Tung | |
| 2016/0083359 | A1 | 3/2016 | Bang-Andersen et al. | |
| 2016/0361275 | A1 | 12/2016 | Gant et al. | |

FOREIGN PATENT DOCUMENTS

| | | |
|---|---|---|
| CN | 1561336 A | 1/2005 |
| CN | 101273024 A | 9/2008 |
| CN | 101336226 A | 12/2008 |
| CN | 10147206 8 | 4/2012 |
| WO | WO 03/029232 A | 4/2003 |

(Continued)

OTHER PUBLICATIONS

Byrn, Stephen. Solid-State Chemistry of Drugs, 2nd Ed. (1999), Ch. 11 Hydrates and Solvates, 233-247.*
Morissette, Sherry. Adv. Drug Delivery Rev. 2004, 56, 275-300.*
Rouhi, Maureen. Chem. & Eng. News, (2003), 81(8), 32-35.*
Banker, Gilbert. Modern Pharmaceutics 3rd ed. Marcel Dekker, Inc. New York, 1996.*
Tonn, G.R. Biological Mass Spectrometry (1993), vol. 22 Issue 11, pp. 633-642.*
Jiang, Wen-Feng et al.: "Application of deuteration in drug research", *Qil u Pharmaceutical Affairs*, 2010, vol. 29, No. 11, pp. 682-684 in Chinese with English abstract.

(Continued)

*Primary Examiner* — Deepak R Rao
*Assistant Examiner* — Laura M Daniel
(74) *Attorney, Agent, or Firm* — McCarter & English, LLP (57) ABSTRACT

The present disclosure provides a deuterium substituted 1-[2-(2,4-dimethyl-phenylsulfanyl)-phenyl]piperazine compound with a structure represented by formula (I) or a derivative thereof, a pharmaceutical composition containing the compound or the derivative thereof, and an application of the compound or the derivative thereof in preparing drugs. The compound can reduce oxidative metabolism thereof, increase the drug concentration in blood and the effective bioavailability, so as to lower the dosage and reduce the toxicity and other side effects. The deuterium 1-[2-(2,4-dimethyl-phenylsulfanyl)-phenyl]piperazine compound and its derivative thereof provided by the present disclosure can be used to treat related diseases such as affective disorders, depression and anxiety.

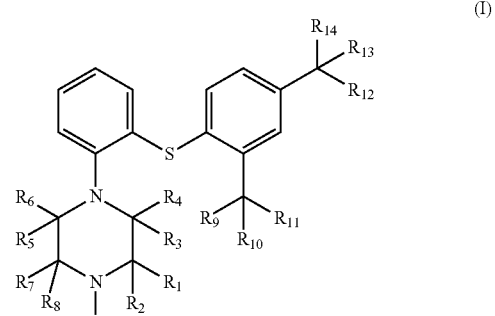

6 Claims, 2 Drawing Sheets

(56) References Cited

FOREIGN PATENT DOCUMENTS

WO    WO 2007/144005 A1    12/2007
WO    WO 2008/113359 A2    9/2008

OTHER PUBLICATIONS

He, Yihui et al.: "Prospects of the parmacological application of heavy water and deuterated drugs", *Foreign Medical Sciences Epidemiology Lemology*, Aug. 2005, vol. 32, No. 4, pp. 255-256 in Chinese with English translation.

International Search Report and Written Opinion issued by Chinese Patent Office, acting as the International Searching Authority, for International Application PCT/CN2014/087662 dated Feb. 17, 2015 in Chinese with English translation.

Wang, Jiang et al.: "Lead compound optimization strategy (1)—changing metabolic pathways and optimizing metabolism stability", *Acta Pharmaceutica Sinica* 2013, 48 (10), pp. 1521-1531 in Chinese with English abstract.

Chen, Grace et al.: "Pharmacokinetic Drug Interactions Involving Vortioxetine (Lu AA21004), a Multimodal Antidepressent", *Clin Drug Investig*, (2013) 33, pp. 727-736.

Bang-Andersen, Benny et al.: "Discovery of 1-[2-)2,4-Dimethylphenylsulfanyl)phenyl]piperazine (LuAA21004): A Novel Multimodal Compound for the Treatment of Major Depressive Disorder", *Journal of Medicinal Chemistry*, 2011, 54, pp. 3206-3221.

Sharma, Raman et al.: "Deuterium Isotope Effects on Drug Pharmacokinetics. I. System-Dependent Effects of Specific Deuteration with Aldehyde Oxidase Cleared Drugs", *Drug Metabolism and Disposition*, vol. 40, No. 3, 2012, pp. 625-634.

Foster, Allan B.: "Deuterium Isotope Eliects in the Metabolism of Drugs and Xenobiotics: Implications for Drug Design", *Advances in Drug Research*, vol. 14, 1985, Academic Press, London, Great Britain, pp. 1-40.

Fisher, Michael, B, et al.: "The complexities inherent in attemptsto decrease drug clearance by blocking sites of CYP-mediated metabolism", *Current Opinion in Drug Discovery & Development*, 2006, vol. 9, No. 1, pp. 101-109.

Extended European Search Report issued by European Patent Office for corresponding application EP 14893470.6 dated Oct. 5, 2017.

* cited by examiner

DEUTERIUM SUBSTITUTED 1-[2-(2,4-DIMETHYL-PHENYLSULFANYL)-PHENYL]PIPERAZINE COMPOUND OR DERIVATIVES THEREOF, AND PHARMACEUTICAL COMPOSITION AND USE THEREOF

CROSS-REFERENCE TO RELATED APPLICATIONS

This application is the National Stage entry under 35 U.S.C. § 371 of International Application No. PCT/CN2014/087662 filed on Sep. 28, 2014, published on Dec. 3, 2015 under publication number WO 2015/180342 A1, which claims the benefit of priority under 35 U.S.C. § 119 of Chinese patent application number 201410244856.3 filed May 30, 2014.

TECHNICAL FIELD

The present disclosure falls in the field of medicine, and relates to a deuterium substituted 1-[2-(2,4-dimethyl-phenylsulfanyl)-phenyl]piperazine compound or derivatives thereof. The derivatives include a pharmaceutically acceptable salt, a solvate, a prodrug, an N-oxide, a polymorph; and their stereoisomer(s), geometrical isomer(s), tautomer(s) and mixture thereof. The present disclosure also relates to a composition comprising the compound or derivatives thereof, and its use in the manufacture of a medicament.

BACKGROUND OF THE INVENTION

Depression is a mental disease, which may lead to physical abnormalities and even to disabilities. In China, the morbidity rate of depression is approximately 3%~5%. According to a prediction from the World Health Organization, depression may become a leading cause of disabilities and/or disease burden by the year 2030.

The symptoms of depression include mood fluctuations and the like, which directly interfere with people's daily life, including their work, study, sleep and diet. The symptoms of depression include loss of interest in daily activities, discomfort, sleep abnormality, susceptibility to fatigue, significant change in body weight, slow thinking, sense of guilt, sense of unworthiness, lack of concentration, and even increased propensity to commit suicide. In fact, not all the patients exhibit the same symptoms.

The etiologies of depression are low levels of monoamine neurotransmitters (e.g. norepinephrine (NE), serotonin (5-HT) and dopamine (DA)) in the central nervous system, and hypofunction of the corresponding receptors. At present, three types of medicaments are available for the treatment of depression. The first type is tricyclic antidepressants (TCAs). They increase the concentrations of NE and 5-HT in the brain, but have drawbacks including severe side effects like cardiotoxicity, additionally their effectiveness has a slow onset. The second type is monoamine oxidase inhibitors (MAOIs). MAOIs have an anti-depression effect that involves retarding the degradation of NE and 5-HT in the brain and thus extending the effective time of these transmitters. The third type is selective serotonin reuptake inhibitors (SSRIs). They increase the concentration of 5-HT in the synaptic cleft by inhibiting the reuptake of 5-HT in the presynaptic membrane, therefore the excitability of the 5-HT1A receptors in the postsynaptic membrane is improved, and concurrently the anti-depression effect is achieved. The advantage of SSRIs is that other neurotransmitter receptors are not affected, and consequently, SSRIs are relatively safe. However, some adverse effects are still observed as a result of non-selective effect on various subtypes of 5-HT receptors.

On Sep. 30, 2013, the U.S. Food and Drug Administration approved a new antidepressant drug named Vortioxetine, which was developed by Lundbeck and Takeda Pharmaceutical Co., Ltd. for treating depression. Its chemical name is 1-[2-(2,4-dimethyl-phenylsulfanyl)-phenyl]piperazine.

Vortioxetine is thought to have an anti-depression effect through its modulation of 5-HT receptors. It was suggested by nonclinical in vivo tests that Vortioxetine can increase the concentrations of neurotransmitters such as asserotonin, norepinephrine, dopamine, acetylcholine and histamine in certain regions of the brain. Nonclinical studies showed that Vortioxetine is able to modulate $5\text{-}HT_3$, $5\text{-}HT_7$, $5\text{-}HT_{1D}$, $5\text{-}HT_{1B}$, $5\text{-}HT_{1A}$, and 5-HT.

Vortioxetine is metabolized primarily through oxidation via cytochrome P450 isoenzymes CYP2D6, CYP3A4/5, CYP2C19, CYP2C9, CYP2A6, CYP2C8 and CYP2B6. Its metabolites are conjugated with glucuronic acid to produce new metabolites. Following a single oral dose of $[^{14}C]$-labeled vortioxetine, approximately 59% and 26% of the radioactive metabolites were recovered in the urine and feces respectively.

When Vortioxetine is administered for treatment, the dosage is often increased in efforts to get desired curing effects, and dose escalation is often accompanied by the unfavorable metabolism of the drug. Since active metabolites produced by unfavorable metabolism are often key reasons for medicament toxicity and other side effects, many adverse reactions would be observed during the use of Vortioxetine for the treatment, including nausea, vomiting, diarrhea, headache, dizziness, etc. Given the foregoing, drugs that reduce the side effects and other toxicity of the antidepressants is an unmet medical need and has attracted broad scientific and medical attentions.

SUMMARY OF THE INVENTION

Technical Problem

The present disclosure is intended to eliminate the defects in the prior art, providing a deuterium substituted 1-[2-(2,4-dimethyl-phenylsulfanyl)-phenyl]piperazine compound or derivatives thereof. The derivatives include a pharmaceutically acceptable salt, a solvate, a prodrug, an N-oxide, a polymorph; and their stereoisomer(s), geometrical isomer(s), tautomer(s) and a mixture thereof. The present disclosure is also intended to provide a composition comprising the compound or its derivatives, and its use in the manufacture of a medicament. The deuterium substituted 1-[2-(2,4-dimethyl-phenylsulfanyl)-phenyl]piperazine compound of the present disclosure as well as a pharmaceutically acceptable acid addition salt thereof show a favorable activity, and solve the unfavorable metabolism problems of the drug, leading to less toxicity and side effects during the application.

Solutions to the Problem

One aspect of the present disclosure is to provide a deuterium substituted 1-[2-(2,4-dimethyl-phenylsulfanyl)-phenyl]piperazine compound or its derivatives thereof. The derivatives include pharmaceutically acceptable salts, solvates, prodrugs, N-oxides, polymorphs; and their stereoisomer(s), geometrical isomer(s), tautomer(s) and a mixture thereof.

Another aspect of the present disclosure is to provide a pharmaceutically acceptable acid addition salt of the deuterium substituted 1-[2-(2,4-dimethyl-phenylsulfanyl)-phenyl]piperazine compound.

Another aspect of the present disclosure is to provide a deuterium substituted 1-[2-(2,4-dimethyl-phenylsulfanyl)-phenyl]piperazine compound in monomorphous or polymorphous form.

Another aspect of the present disclosure is to provide a pharmaceutical compositon, comprising: the deuterium substituted 1-[2-(2,4-dimethyl-phenylsulfanyl)-phenyl]piperazine compound, or a pharmaceutically acceptable salt, a solvate, a prodrug, an N-oxides, a polymorph thereof, and their stereoisomer(s), geometrical isomer(s) or tautomer(s) or a mixture thereof; and one selected from pharmaceutically acceptable carrier, excipient, diluent, adjuvant and media, or a combination thereof.

Another aspect of the present disclosure is to provide the use of the deuterium substituted 1-[2-(2,4-dimethyl-phenylsulfanyl)-phenyl]piperazine compound, or a pharmaceutically acceptable salt, a solvate, a prodrug, a N-oxide, a polymorph, and their stereoisomer, geometrical isomer, tautomer or a mixture thereof, in the manufacture of a medicament for treating a disease. The disease is selected from depression, flush, affective disturbance, sleep apnea, anxiety, attention deficit hyperactivity disorder (ADHD), post-traumatic stress disorder (PTSD), irritable bowel syndrome (IBS), alcoholism, nicotine addiction, drug addiction and drug abuse.

Effects of the Technology

The deuterium substituted 1-[2-(2,4-dimethyl-phenylsulfanyl)-phenyl]piperazine compound of the present disclosure is superior to 1-[2-(2,4-dimethyl-phenylsulfanyl)-phenyl]piperazine in the prior art in that:

(1) The compound of the present disclosure has better curing effects. The compound is able to reduce the unfavorable metabolism and increase the concentration of the medicament in the blood, thus improved efficacy is achieved.

(2) The compound of the present disclosure can increase the bioavailability of the drug, reduce the undesired metabolism in the intestine's internal wall and the liver (which is known as "first-pass metabolism"), which leads to a higher ratio of the unmetabolized drug reaching the target sites.

(3) The compound of the present disclosure exhibits less toxicity and side effects. The metabolites produced by unfavorable metabolism of a drug are often an important factor in drug related toxicity and other side effects. With less unfavorable metabolism, the toxicity and other side effects of the drug may also be significantly reduced.

"Metabolism product" refers to a product obtained by in vivo metabolism of a specific compound or a salt thereof. The metabolites of a compound can be identified by known techniques, and its activity can be characterized through conventional tests. Such a product can be obtained through oxidation, reduction, hydrolysis, amidation, deamidation, esterification, de-esterification, enzyme cleavage, etc., of the administered compound. Correspondingly, the metabolites of the compound of the present disclosure also include those metabolites produced by the compound of the present disclosure in full contact with a mammal after a period of time.

DETAILED DESCRIPTION OF THE INVENTION

The present disclosure is implemented through the technical solutions given below.

A deuterium substituted 1-[2-(2,4-dimethyl-phenylsulfanyl)-phenyl]piperazine compound with a structure of the following formula (I), or its derivatives thereof, and the derivatives include a pharmaceutically acceptable salt, a solvate, a prodrug, an N-oxide, and their stereoisomer(s), geometric isomer(s), tautomer(s) and a mixture thereof:

wherein $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ are each independently a hydrogen atom or a deuterium atom, provided that at least one of them is a deuterium atom.

The aforesaid deuterium substituted 1-[2-(2,4-dimethyl phenylsulfanyl)phenyl]piperazine compound or the derivatives thereof, wherein one or more of $R_1$, $R_2$, $R_3$, $R_4$, $R_5$, $R_6$, $R_7$ and $R_8$ is/are a deuterium atom/deuterium atoms.

The aforesaid deuterium substituted 1-[2-(2,4-dimethyl phenylsulfanyl)phenyl]piperazine compound or the derivatives thereof, wherein one or more of $R_9$, $R_{10}$, $R_{11}$, $R_{12}$, $R_{13}$ and $R_{14}$ is/are a deuterium atom/deuterium atoms.

The derivative of the aforesaid deuterium substituted 1-[2-(2,4-dimethyl-phenylsulfanyl)-phenyl]piperazine compound is a pharmaceutically acceptable acid addition salt, and said pharmaceutically acceptable acid addition salt is preferably an addition salt with hydrobromic acid.

The aforesaid deuterium substituted 1-[2-(2,4-dimethyl-phenylsulfanyl)-phenyl]piperazine compound or derivatives thereof is in monomorphous or polymorphous form.

A pharmaceutical composition, comprising the aforesaid compound or a derivative thereof; and one selected from a pharmaceutically acceptable carrier, excipient, diluent, adjuvant and medium, or a combination thereof.

The use of the compound or a derivative thereof in the manufacture of a medicament for treating a disease, wherein the disease is selected from depression, flush, affective disturbance, sleep apnea, anxiety, attention deficit hyperactivity disorder (ADHD), post-traumatic stress disorder (PTSD), chronic pain, irritable bowel syndrome (IBS), alcoholism, nicotine addiction, vomiting, drug addiction and drug abuse.

The deuterium substituted 1-[2-(2,4-dimethyl-phenylsulfanyl)-phenyl]piperazine compound is preferably a compound selected from the following examples:

PREFERRED EXAMPLE 1

1-[2-(2-methyl-4-trideuteriomethylphenylsulfanyl)phenyl]piperazine

PREFERRED EXAMPLE 2

1-{2-[2,4-bis(trideuteriomethyl)phenylsulfanyl]phenyl}piperazine

PREFERRED EXAMPLE 3

1-[2-(2-methyl-4-dideuteriomethyl-phenylsulfanyl)phenyl]piperazine

PREFERRED EXAMPLE 4

1-{2-[2,4-bis(monodeuteriomethyl)phenylsulfanyl]phenyl}piperazine

PREFERRED EXAMPLE 5

1-[2-(2-monodeuteriomethyl-4-trideuteriomethyl-phenylsulfanyl)phenyl]piperazine

PREFERRED EXAMPLE 6

1-[2-(2-methyl-4-trideuteriomethyl-phenylsulfanyl)phenyl]octodeuteriopiperazine

PREFERRED EXAMPLE 7

1-{2-[2,4-bis(trideuteriomethyl)phenylsulfanyl]
phenyl}octodeuteriopiperazine

In the present disclosure, the term "deuterium substituted" means one or more hydrogen atom(s) in a compound or a group is/are substituted by deuterium atom(s). Deuterium substitution means any number, e.g. one, two or more, or all of the hydrogen atoms are replaced. The content of deuterium at the deuterium substitution position is at least greater than its natural abundance (0.015%), preferably greater than 30%, more preferably greater than 50%, further more preferably greater than 75%, still further more preferably greater than 95%, and particularly preferably greater than 99%. The term "substituted by one or more deuterium atom(s)" and "substituted by deuterium atom(s) one or more times" can be used interchangeably.

Generally speaking, the term "substituted" means that one or more of hydrogen atoms in a given structure may be replaced by a specific group. An optional substituent group may be substituted by a substituent at any replaceable sites of the group, unless otherwise stated. When more than one site of a given structure can be replaced by one or more substituent(s) selected from specific groups, all those sites may be replaced by the same or different groups. The term "hydrogen" means a single hydrogen atom. The term "deuterium" means a single deuterium atom. With one such atom on a methyl group, a monodeuterated methyl group (—CDH$_2$) is formed. With two deuterium atoms on a methyl group, a dideuterated methyl group (—CD$_2$H) is formed. With three deuterium atoms on a methyl group, a trideuterated methyl group (—CD$_3$) is formed.

The term "solvate" means a physical association of the compound of the present disclosure with one or more kinds of solvent molecules. The physical association involves ionic and covalent binding in any degree, as well as hydrogen bonding. In some cases, for example, where one or more kinds of solvent molecules are incorporated into lattices of a crystalline solid, the solvate can be separated. A "solvate" contains the solution phase and the separable solvate. The nonrestrictive examples of solvate include ethanol solvate and methanol solvate. A "hydrate" is a solvate in which the solvent molecule is H$_2$O. A solvate can be prepared using a known method. A typical but nonrestrictive method comprises the steps of: dissolving the compound of the present disclosure in required solvent of required amount (an organic solvent, water, or a mixture thereof) at a temperature higher than ambient temperature; cooling the solution at a rate which is sufficient for crystal formation, and separating the crystal according to a standard method. An analytical technique such as infrared spectrometry may be adopted to prove the existence of solvent (or water) in a crystal as a solvate (or a hydrate).

The term "prodrug" represents a substance which can be converted in vivo into deuterium substituted 1-[2-(2,4-dimethyl-phenylsulfanyl)-phenyl]piperazine or derivatives thereof (for example, a drug precursor). The conversion may take place through various mechanisms (e.g. through metabolism or chemical treatment). For example, it may occur through hydrolysis in the blood. Discussions about the use of prodrugs are provided in *Pro-drugs as Novel Delivery Systems* from A.C.S. *Symposium Series* (volume 14) by T. Higuchi and W. Stella, and in *Bioreversible Carriers in Drug Design from American Pharmaceutical Association and Pergamon Press*, 1987, edited by Edward B. Roche. A prodrug of the compound of the present disclosure may be formed by e.g. substituting the hydrogen atoms of the amine groups with appropriate groups.

The term "stereoisomer" in the present disclosure includes all the pure enantiomers/stereoisomers and enriched enantiomers/stereoisomers of the compounds of the present disclosure.

The deuterium substituted 1-[2-(2,4-dimethyl-phenylsulfanyl)-phenyl]piperazine compound of the present disclosure or its pharmaceutically acceptable acid addition salt may be an active component of a pharmaceutical composition for treating severe depressive disorder and general anxiety disorder. The pharmaceutical composition may contain an effective amount of the compound or its pharmaceutically acceptable acid addition salt; and one selected from a pharmaceutically acceptable carrier, excipient, diluent, adjuvant and medium, or a combination thereof. The pharmaceutical composition may be made into a dosage form suitable for use. The drug delivery system may be an albumin-bound injection, liposome, powder injection, nanoparticle or cyclodextrin inclusion complex. The dosage form for administration may be an injectable solution, or a solid or semisolid form, for example injection, tablet, capsule, pill, powder or granule and the like.

The pharmaceutically acceptable carrier, adjuvant or medium that can be used in pharmaceutical composition according to the present disclosure includes but is not limited to the serum proteins of human serum albumin, lecithin, disodium hydrogen phosphate, sodium chloride, potassium hydrogen phosphate, colloidal silicon dioxide, magnesium trisilicate, polyvinyls, cellulose-based material, polyethylene glycol, sodium carboxymethyl cellulose, polyacrylate, polyethylene-polyoxypropylene block polymer, polyethylene glycol, aluminium oxide, aluminium stearate, phosphate, glycine, sorbic acid, potassium sorbate, a partial glyceride mixture, water, a salt, and an electrolyte.

The deuterium substituted 1-[2-(2,4-dimethyl-phenylsulfanyl)-phenyl]piperazine compound of the present disclosure may be made into be a pharmaceutically acceptable salt suitable to be a medicament. A pharmaceutically acceptable salt suitable to be a medicament refers to a salt suitable to be a medicament that is formed from the compound of the present disclosure with a non-toxic acid or alkali, including inorganic and organic salts. A preferred salt is a salt that is formed from the compound of the present disclosure with an acid. The acid suitable for the formation of the salt includes but is not limited to, an inorganic acid, e.g. hydrobromic acid, hydrochloric acid, hydrofluoric acid, sulfuric acid, nitric acid and phosphoric acid. The salt may also be formed with an organic acid, including formic acid, acetic acid, propionic acid, oxalic acid, malonic acid, cinnamic acid, citraconic acid, succinic acid, fumaric acid, maleic acid, lactic acid, malic acid, tartaric acid, citric acid, picric acid, methane sulfonic acid, benzene methane sulfonic acid, benzoic acid, ascorbic acid, methylenedisalicylic acid, ethionic acid, salicylic acid, gluconic acid, mandelic acid, aspartic acid, stearic acid, palmitic acid, glycollic acid, 4-aminobenzoic acid, glutamic acid, benzene sulfonic acid, succinic acid and theophylline-7-acetic acid, as well as an acidic amino acid such as itaconic acid and aspartic acid.

All the stereoisomers, geometric isomers, tautomers, nitrogen oxides, hydrates, solvates, metabolites, pharmaceutically acceptable salts and prodrugs fall in the scope of the present application, unless otherwise stated.

The pharmaceutical composition of the present disclosure can be administered orally, injected, inhaled as spray, locally, rectally, nasally, buccally, vaginally, or through an implanted drug reservoir. The pharmaceutical composition is preferably administered orally, intraperitoneally, or by intravenous injection.

The sterile injection of the pharmaceutical composition of the present disclosure may be an aqueous or an oleaginous suspension. The suspension can be prepared with conventional technologies using appropriate dispersant, wetting agent and suspending agent according to a formulation.

The pharmaceutical composition of the present disclosure may be a solid, including but not limited to capsule, tablet, pill, granule, powder and suppository. The pharmaceutical composition of the present disclosure may be a liquid, including but not limited to solution, suspension and emulsion.

According to known methods in the art, a solid dosage form e.g. tablet, sugary pill, capsule, pill and granules, may be film coated or enteric coated. A extended release material may be used, including but not limited to glycerin monostearate and glycerin distearate.

The pharmaceutical composition of the present disclosure may be a tablet or a capsule, comprising: an active ingredient; a diluent, including but not limited to lactose, dextrose, sucrose, mannitol, sorbitol, cellulose and/or glycine; a lubricant, including but not limited to silicon dioxide, talc, stearic acid, stearate and polyethylene glycol.

The pharmaceutical composition of the present disclosure may be a tablet, comprising an adhesive, including but not limited to magnesium aluminosilicate, starch paste, gelatin, tragacanth gum, methylcellulose, and sodium carboxymethyl cellulose. Carriers for an oral tablet usually include lactose and corn starch. A lubricant such as magnesium stearate is typically added. The composition may also contain a disintegrant, an adsorbent, a colorant, a flavoring agent and a sweetener, or may contain an ordinary inert diluent, and an adjuvant such as preservative, stabilizer, wetting agent, emulsifier and buffer.

For a capsule to be administered orally, the suitable diluents may include lactose or dry corn starch. When an aqueous suspension is to be orally administered, the active ingredients include an emulsifier and a suspending agent.

The pharmaceutical composition of the present disclosure may be in the form of discrete units. The discrete unit form may be an aqueous solution or suspension; a nonaqueous solution or suspension; a water-in-oil liquid emulsion, an oil-in-water liquid emulsion; or embedded in liposomes, or pills.

The pharmaceutical composition of the present disclosure may be subjected to an ordinary pharmaceutical process, e.g. sterilization.

In one embodiment, the compound or the pharmaceutically acceptable acid addition salt of the present disclosure is a crystal. For an oral tablet, preferably the active ingredient is a crystal.

In one embodiment, the compound of the present disclosure may be in the form of a crystal.

In one embodiment, the present disclosure provides a pharmaceutical composition, comprising 1 to 10 parts of HBr salt of compound (I), 10 to 50 parts of microcrystalline cellulose, 10 to 25 parts of corn starch, 1 to 10 parts of sodium starch glycolate, 1 to 5 parts of talc, 30 to 45 parts of anhydrous dicalcium phosphate and 0.5 to 5 parts of magnesium stearate. The therapeutically effective dose of the compound, the pharmaceutical composition or combination thereof depends on the race, body weight, age of the individual, the condition of the individual, the treatment obstacles or diseases to be treated and their severity levels. Physicians and clinicians may adjust the effective dose of each active ingredient in accordance with the prevention, treatment, or inhibitive purpose or the progress of the disease.

The deuterium substituted 1-[2-(2,4-dimethyl-phenylsulfanyl)-phenyl]piperazine compound or the pharmaceutically acceptable acid addition salt of the present disclosure, as an active ingredient of a pharmaceutical composition, can be used to treat a depressive disease, including depression, flush, affective disturbance, sleep apnea, anxiety, attention deficit hyperactivity disorder (ADHD), post-traumatic stress disorder (PTSD), irritable bowel syndrome (IBS), alcoholism, nicotine addiction, vomiting, drug addiction and drug abuse.

The compound of the present disclosure may be solely administered or administered in combination with other pharmaceutically acceptable compounds.

When used in a pharmaceutical composition, the compound of the present disclosure is applied to a mammal (e.g. human being) in need of treatment in a safe and effective dose. The applied dosage is an amount considered as effective in pharmaceutical practice. For a person weighting 60 kg, the daily dosage is usually 1 to 2000 mg, preferably 2 to 1000 mg, further preferably 5 to 100 mg. The specific dosage should be determined in consideration of the administration route, the patient's health condition and other clinical parameters.

Deuterium is an isotope of hydrogen. As a stable form isotope of hydrogen, the nucleus of deuterium consists of one proton and one neutron, i.e. one more neutron comparing with hydrogen nucleus (the atomic weight of deuterium=2, while the atomic weight of hydrogen=1). It makes the "deuterium-carbon" bond more stable than the "hydrogen-carbon" bond (the cleavage rate of C—H bond is six times faster than that of C-D bond). Deuterium is neither toxic nor radioactive, so it is safe to human beings. The present applicants found that some deuterium-substituted drugs behaved differently in human bodies. Since the "deuterium-carbon" bond is stronger than "hydrogen-carbon" bond, it may influence the decomposition rates of drugs. In other words, the replacement of hydrogen at specific sites of a drug by deuterium may block the metabolic sites, thus prolonging the half-life of the drug without adversely affecting its pharmacological activity. At specific sites, i.e. the unfavorable metabolic sites of Vortioxetine structure, the "hydrogen-carbon" bond is replaced by "deuterium-carbon" bond; since the "deuterium-carbon" bond is more stable than the "hydrogen-carbon" bond, the compound is less readily metabolized. Thus the hydrobromide salt of 1-{2-[2,4-bis(trideuteriomethyl)phenylsulfanyl]phenyl}piperazine of the present disclosure is decomposed slowly in the body, and the unfavorable metabolism of the drug is reduced; the half-life of the drug is prolonged, while the plasma concentration of the drug is increased, therefore a better therapeutic effect is achieved. In addition, since the therapeutic effect is maintained, the dosage of the drug used may be reduced; this may further reduce the toxicity and side effect(s) of the drug.

The present applicants found that some hydrogen atoms in the structure of hydrobromide salt of 1-{2-[2,4-bis(trideuteriomethyl)phenylsulfanyl]phenyl}piperazine, e.g. those from $R_{12}$, $R_{13}$ and $R_{14}$, correspond to the hydrogen atoms at the unfavorable metabolic sites of Vortioxetine. So deuterium substitution targeting these sites may further improve the in vivo stability of the drug in the organism, and increase the plasma concentration of the drug, leading to better therapeutic effects. Test results demonstrated that in comparison with Vortioxetine, 1-{2-[2,4-bis(trideuteriomethyl) phenylsulfanyl]phenyl}piperazine hydrobromic acid salt, i.e. where $R_9$, $R_{10}$, $R_{11}$, $R_{12}$, $R_{13}$ and $R_{14}$ are deuterium atoms, had dramatically improved concentration in the plasma, increased stability and dramatically increased absolute bioavailability; It had better pharmacokinetic profiles in animals, and achieved better pharmacodynamics and therapeutic effects.

The methods of preparing the compound represented in formula (I) will be described below in more detail. Those methods should not be interpreted to limit the present disclosure. The compounds of the present disclosure can be conveniently made using a method which is a combination of the methods described in this specification or those known in this field. A person skilled in the art can easily make such a combination.

EXAMPLE 1

Figure 1:
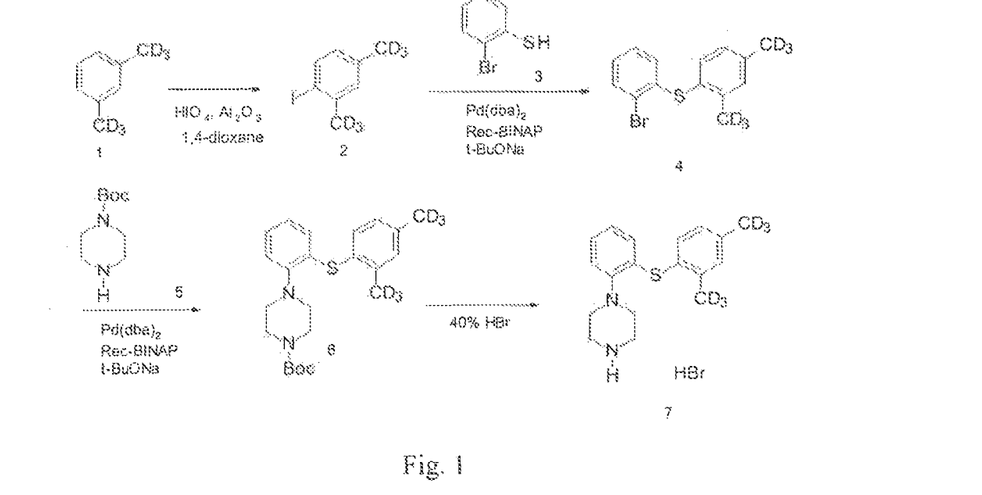
FIG. 1 shows a reaction formula for preparing 1-{2-[2,4-bis(trideuteriomethyl)phenylsulfanyl]phenyl}piperazine and its hydrobromide salt thereof.

Preparation of 1-{2-[2,4-bis(trideuteriomethyl)phenylsulfanyl]phenyl}piperazine and its Hydrobromic Acid Salt Thereof The reaction formula is shown in FIG. 1.
The preparation includes the following steps:

Step I: Preparation of 2,4-bis(trideuteriomethyl)iodobenzene (Compound 2)

At ambient temperature, 1,4-dioxane (85 mL), $Al_2O_3$ (40.74 g, 399.6 mmol) and solution of periodic acid (20.33 g, 89.2 mmol) in water (20.33 g) were added sequentially into a 250-mL 3-neck flask under stirring. The reaction proceeded for 4 hr after the temperature was raised to 85° C. to give a sepia solution. A solution of 1,3-bis(trideuteriomethyl)benzene (Compound 1) (2.00 g, 17.84 mmol) in 1,4-dioxane (25 mL) was added to the above solution. The reaction continued at the same temperature for about 45 min until Compound 1 was consumed as evidenced by GC-MS.

The reaction system was cooled to ambient temperature, and subjected to suction filtration. The filtration cake was rinsed with methyl tert-butyl ether (100 mL×3). The filtrate was transferred to a separating funnel and washed with a saturated $NaHSO_3$ solution (200 mL×3). The organic phase was separated out, and the aqueous phase was extracted with methyl tert-butyl ether (200 mL×1). All the organic phases were combined, washed with water (200 mL×3), dried over anhydrous $Na_2SO_4$, filtrated, and concentrated at 30° C. to afford the title product as yellow oil (4.11 g, 96.82%). The crude product 2,4-bis(trideuteriomethyl)iodobenzene (Compound 2) was used in the next step without purification.

GC-MS: m/z 238 ($M^+$); $^1$H-NMR (300 MHz, $CDCl_3$) δ 8.01 (d, J=8.1 Hz, 1H), 7.12-7.06 (m, 1H), 6.73-6.70 (m, 1H).

Step II: Preparation of 2-[2,4-bis(trideuteriomethyl)phenylsulfanyl]bromobenzene (Compound 4)

Toluene (70 mL), Compound 2 (4.11 g, 17.27 mmol), Compound 3 (3.26 g, 17.27 mmol), rac-BINAP ((+/−)-2,2'-bis(diphenylphosphino)-1,1'-binaphthyl, 0.398 g, 0.639 mmol), $Pd(dba)_2$ (tris(dibenzylideneacetone)dipalladium, 0.285 g, 0.31 mmol) and t-BuONa (5.81 g, 60.45 mmol) were added sequentially to a 100-mL 3-neck flask under stirring at ambient temperature. The reaction system was subjected to $N_2$ purge (about 5 min×3), and was heated to 100° C. under $N_2$ protection. One hour later, thin layer chromatography (TLC) suggested the end of the reaction. 50 mL of water was added to quench the reaction after the system was cooled to ambient temperature. The reaction system was subjected to suction filtration with diatomite. The filtration cake was washed with ethyl acetate (100 mL×3). The filtrate was transferred to a separating funnel to separate out the organic phase. The aqueous phase was subjected to extraction with ethyl acetate (50 mL×2). The organic phases were combined, dried over anhydrous $Na_2SO_4$, filtrated and subjected to vacuum concentration to afford 7.2 g the crude product as a brown oil. The crude product was purified by silica gel column chromatography (hexane as the eluent), leading to the title product as a colorless oil (4.64 g, with a yield of 89.92%).

HPLC: ~100%; $^1$H-NMR (300 MHz, $CDCl_3$) δ 7.54 (d, J=7.8 Hz, 1H), 7.4 (d, J=7.8 Hz, 1H), 7.19 (d, J=1.5 Hz, 1H), 7.11-7.06 (m, 1H), 7.00-6.95 (m, 1H), 6.97-6.58 (m, 1H), 6.55 (d, J=1.2 Hz, 1H).

Step III: Preparation of 1-Boc-{2-[2,4-bis(trideuteri-omethyl)phenylsulfanyl]phenyl}piperazine (Compound 6)

Step IV: Preparation of 1-{2-[2,4-bis(trideuteriom-ethyl)phenylsulfanyl]phenyl}piperazine and its Hydrobromic Acid Salt Thereof (Compound 7)

Toluene (30 mL), Compound 4 (4.64 g, 15.52 mmol), Boc-piperazine (Compound 5, 8.67 g, 46.56 mmol), rac-BINAP (1.353 g, 2.17 mmol) and t-BuONa (5.22 g, 54.32 mmol) were added sequentially to a 100-ml 3-neck flask under stirring at ambient temperature. Pd(dba)$_2$ (1.02 g, 1.12 mmol) was added to the above reaction system under N$_2$ protection. The system was heated to 50° C., and the reaction proceeded for 1 hr (TLC suggested that about 50 percent of the raw materials remained at this point). The system was heated to 80° C., and the reaction proceeded for 5 hr (TLC suggested that about 10 percent of the raw materials remained at this point). The reaction system was cooled to ambient temperature, quenched with water (50 mL) and subjected to suction filtration with diatomite. The filtration cake was washed with ethyl acetate (100 mL×2). The filtrate was transferred to a separating funnel to separate out the organic phase. The aqueous phase was subjected to extraction with ethyl acetate (50 mL×2). The organic phases were combined, dried over anhydrous Na$_2$SO$_4$, filtrated and subjected to vacuum concentrating, resulted in brown oil (15 g). The crude product was purified by silica gel column chromatography (hexane/ethyl acetate=1/40 as the eluent), leading to the title product as a yellow solid (3.93 g, with a yield of 65.8%).

HPLC: 93.6%; $^1$H-NMR (300 MHz, CDCl$_3$) δ 7.39 (d, J=7.8 Hz, 1H), 7.17 (s, 1H), 7.09-7.03 (m, 3H), 6.92-6.87 (m, 1H), 6.54 (d, J=8.1 Hz, 1H), 3.65-3.62 (t, J=4.8 Hz, 4H), 3.04-3.01 (t, J=4.5 Hz, 4H), 1.51 (s, 9H).

Diethyl ether (97.2 mL) and Compound 6 (3.24 g, 8.02 mmol) were added sequentially to a 250 mL single neck flask in a water bath under stirring at ambient temperature with N$_2$ as the protective gas. A 40% HBr solution (4.87 g, 24.06 mmol) was added dropwise to the above system over 15 min. The reaction proceeded for 6 hr at ambient temperature (TLC suggested that a few of the raw materials remained at this point). The stirring was stopped, and the reaction system was left to stand still for several minutes. The upper clear liquid was separated out. Diethyl ether (10 mL×2) was added to the resultant viscous solid, followed by ultrasonic processing. The mixture was left to stand still. The upper clear liquid was separated out. Isopropanol (4.5 mL) was added to the resultant solid, followed by stirring for 5 min at ambient temperature. 20 mL of diethyl ether was further added to the system, followed by stirring at ambient temperature for 10 min and then by suction filtration. The filtration cake was washed with diethyl ether (10 mL×3) and dried at ambient temperature, leading to the title product as a white powder (2.4 g, with a yield of 77%).

HPLC: 99.8%; LC-MS (ESI$^+$): m/z 305.28 (M+H); $^1$H-NMR (300 MHz, CD$_3$OD) δ 7.34 (d, J=7.8 Hz, 1H), 7.24 (s, 1H), 7.24-7.17 (m, 2H), 7.12-7.09 (m, 1H), 6.56 (d, J=7.5 Hz, 1H), 3.42-3.39 (m, 4H), 3.33-3.30 (m, 4H). $^{13}$C-NMR (75 MHz, CD$_3$OD): 149.1, 143.0, 140.8, 136.8, 135.6, 132.8, 129.0, 128.8, 127.8, 127.2, 126.6, 121.5, 49.7, 45.4.

EXAMPLE 2

Preparation of 1-[2-(2-methyl-4-tridenteriomethyl-phenylsulfany0phenyl]piperazine and its hydrobromic acid salt thereof The preparation method is as same as that in Example 1, except that 1,3-bis(trideuteriomethyl)benzene in step I was replaced by 3-(trideuteriomethyl)toluene.

Reference for the preparation of 3-(trideuteriomethyl) toluene, Kwa, T. L. and Boelhouwer, C. *Tetrahedron* (1969), 25 (24), 5771-6.

EXAMPLE 3

Preparation of 1-[2-(2-methyl-4-dideuteriomethyl-phenylsulfanyl)phenyl]piperazine and its Hydrobromic Acid Salt Thereof The preparation method is as same as that in Example 1, except that 1,3-bis(trideuteriomethyl)benzene in step I was replaced by 3-(dideuteriomethyl)toluene.

See *Journal of the Chemical Society, Faraday Transactions* (1994), 90 (4), 659-65, by Harper, Robert J. and Kemball, Charles for the preparation of 3-(dideuteriomethyl)toluene.

EXAMPLE 4

Preparation of 1-{2-[2,4-bis(monodeuteriomethyl) phenylsulfanyl]phenyl}piperazine and its Hydrobromic Acid Salt Thereof The preparation method is as same as that in Example 1, except that 1,3-bis(trideuteriomethyl)benzene in step I was replaced by 1,3-bis(monodeuteriomethyl)benzene.

See *Journal of Organic Chemistry* (1973), 38 (8), 1491-6, by Trimitsis, George B., Tuncay, A., Beyer, R. D., and Ketterman, K. J. for the preparation of 1,3-bis(monodeuteriomethyl)benzene.

EXAMPLE 5

Preparation of 1-[2-(2-monodeuteriomethyl-4-trideuteriomethylphenylsulfanyl)phenyl]piperazine and its Hydrobromic Acid Salt Thereof The preparation method is as same as that in Example 1, except that 1,3-bis(trideuteriomethyl)benzene in step I was replaced by 2-monodeuteriomethyl-4-trideuteriomethylbenzene.

See *Journal of the Chemical Society, Faraday Transactions* (1994), 90 (4), 659-65, by Harper, Robert J. and Kemball, Charles for the preparation of 2-monodeuteriomethyl-4-trideuteriomethyl-benzene.

EXAMPLE 6

Preparation of 1-[2-(2-methyl-4-trideuteriomethyl-phenylsulfanyl)phenyl]octodeuteriopiperazine and its Hydrobromic Acid Salt Thereof The preparation method is as same as that in Example 1, except that 1,3-bis(trideuteriomethyl)benzene in step I was replaced by 1-methyl-3-trideuteriomethylbenzene, and that Boc-piperazine (Compound 5) in step III was replaced by Boc-piperazine-D8, a commercially available product.

EXAMPLE 7

Preparation of 1-{2-[2,4-bis(trideuteriomethyl)phenylsulfanyl]phenyl}octodeuteriopiperazine and its Hydrobromic Acid Salt Thereof The preparation method is as same as that in Example 1, except that Boc-piperazine (Compound 5) in step III was replaced by Boc-piperazine-D8, a commercially available product.

<Antidepression Effects>

The following method is used for testing the antidepression effect of the compound of the present application. ICR mice or SD rats, gavaged for two successive weeks, were subjected to mice swimming test, mice tail suspension test and rats swimming test. See below for details of the tests and results.

Mice Swimming Test

Male ICR mice weighing 18 g to 20 g were used. They were fed on sterilized standard feed.

The compound administered in the test was 1-{2-[2,4-bis(trideuteriomethyl)phenylsulfanyl]phenyl}piperazine hydrobromic acid salt (XX for short). Vortioxetine (YY for short) was used as a control sample. Venlafaxine HCl (from Wyeth, USA) was used as a positive control.

Vortioxetine (15 mg) was combined with 10% hydroxypropyl-β-cyclodextrin to form a solution of 100 mL and was administered at daily dose of 3 mg/kg. 1-{2-[2,4-bis(trideuteriomethyl)phenylsulfanyl]phenyl}piperazine hydrobromic acid salt (15 mg and 7.5 mg) was combined with 10% hydroxypropyl-β-cyclodextrin to form two solutions of 100 mL and was administered at daily doses of 3 mg/kg and 1.5 mg/kg, respectively. Venlafaxine HCl (75 mg) was combined with 0.5% CMC-Na to form a solution of 100 mL and was administered at daily dose of 30 mg/kg.

A recording and analysis system for small-animal behavior (Noldus) was used.

See below for details of the test.

I. Prescreening for Swimming Test

All the eighty mice were subjected to prescreening one day before the administration. The mice, fasted for 4 hours were put in a round glass tank (ø 14 cm×h 20 cm, with water of 10 cm depth and at a temperature of 25° C.) to swim. Those mice that did not move for 70 to 160 seconds during 6 min were selected for testing the next day. The whole swimming course was recorded by the video and the data were collected and analyzed automatically by Noldus software.

II. Grouping and Administration Scheme

The forty qualified mice were divided into 4 groups, each of which had 10 mice, according to the Excel random grouping.

| Group 1 | blank control | 10% hydroxypropyl-β-cyclodextrin |
| Group 2 | YY control | 3 mg/kg |
| Group 3 | XX medium dosage | 3 mg/kg |
| Group 4 | XX low dosage | 1.5 mg/kg |

III. Test Method

The medicaments were administered to each group by gavage with the amount of 0.2 ml per 10 g of body weight, once a day for 14 successive days. One hour later after the last oral administration, the mice were allowed to swim for 6 min. The video recorded the whole swimming course, and the Noldus software automatically collected and analyzed the data. The length of time that the mice did not move within the last 4 min was recorded.

The data was given as "average±standard deviation" ($\bar{x}$±s). One-way analysis of variance (one-way ANOVA) was used for data difference statistics. Differences among the groups were determined by P<0.05.

Results

The gavage administration of 30 mg/kg of positive control Venlafaxine for two successive weeks markedly shortened the length of time that the mice stopped swimming (P<0.05 v.s the blank control), which suggested that the test method was reliable. 3 mg/kg of the YY control did not shorten the length of time that the mice stopped swimming, which suggested that the dosage of YY had no antidepressive effect in the mice swimming test. Both 1.5 mg/kg of XX and 3 mg/kg of XX markedly shortened the length of time that the mice did not move ((P<0.05 v.s the blank control). See Table 1 for details.

TABLE 1

Effects of XX sample on mice swimming test, which is administered by gavage for successive 14 days (n = 10, $\bar{x}$ ± s).

| Group Name | Dosage | Duration without Movement within the Last 4 min of the Whole 6 min (s) |
|---|---|---|
| blank control | 10% hydroxypropyl-β-CD | 204.6 ± 18.7 |
| Venlafaxine | 30 mg/kg | 173.6 ± 31.4* |
| YY | 3 mg/kg | 199.6 ± 26.1 |
| XX medium dosage | 3 mg/kg | 176.3 ± 37.5* |
| XX low dosage | 1.5 mg/kg | 173.4 ± 36.1* |

*P < 0.05, compared with blank control

Mice Tail Suspension Test

The animals, medicaments, calculation of dosages to the mice, preparation of drug solution and apparatus are the same as those in the mice swimming test.

Test Method

The medicaments were correspondingly administered by gavage, once a day, to the animals in the groups for 14 successive days, with the amount of 0.2 ml per 10 g of body weight. The mice were subjected to tail suspension one hour later after the last oral administration. The suspension continued for 6 min. The length of time that the mice did not move within 6 min was recorded.

The data was given as "average±standard deviation" ($\bar{x}$±s). One-way analysis of variance (ANOVA) was used for data difference statistics. Differences among the groups were determined by P<0.05.

Results

Being similar to the mice swimming test, the continuous gavage administration of 30 mg/kg of Venlafaxine for two successive weeks markedly shortened the length of time that the tail-suspended mice stopped moving (P<0.01 v.s the blank control), which suggested that the test method was reliable. 3 mg/kg of the YY control likewise did not shorten the length of time that the tail-suspended mice stopped moving, which suggested that with such dosage, YY had no antidepressive effect in the mice tail suspension test. 3 mg/kg of XX markedly shortened the length of time that the tail-suspended mice did not move ((P<0.01 v.s the blank control) and 1.5 mg/kg of XX also showed a tendency to shorten the length of time that the tail-suspended mice did not move. See Table 2 for details.

TABLE 2

Effects of XX sample on mice tail-suspension test, which is administered by gavage for successive 14 days (n = 10, $\bar{x} \pm s$).

| Group Name | Dosage | Duration without Move within 6 min (s) |
|---|---|---|
| blank control | 10% hydroxypropyl-β-CD | 259.4 ± 51.5 |
| Venlafaxine | 30 mg/kg | 180.6 ± 661.8** |
| YY control | 3 mg/kg | 284.9 ± 51.2 |
| XX medium dosage | 3 mg/kg | 152.9 ± 35.4** |
| XX low dosage | 1.5 mg/kg | 212.6 ± 54.9 |

**$P < 0.01$, compared with blank control

Rats Swimming Test

Animals

Male SD rats weighing 200 to 220 g were used and they were fed with sterilized standard feed. The medicaments were the same as those in the mice tail suspension test, but the dosage administered to rats was half of that to mice.

Drug solution preparation: Since the dosage applied on rats was 1 ml/100 g body weight, the medicament solutions used in this test had the same concentrations as those used on mice.

The apparatus was the same as that in the rats swimming test.

Test Details

I. Pre-Swimming of the Rats

The rats were fasted for 4 hours, put in a round glass tank (ø 18 cm×h 40 cm, with water of 15 cm depth and at a temperature of 25° C.), and were allowed to swim for 15 min. One tank accommodated one rat at a time. The tank was refilled with clean water for another rat after one rat finished swimming. The rats were dried with a hot-air blower after swimming.

II. Grouping and Administration Dosage

The forty rats were divided into 4 groups, each of which has 10 rats, according to the Excel random grouping.

| Group 1 | blank control | 10% hydroxypropyl-β-cyclodextrin |
| Group 2 | YY control | 1.5 mg/kg |
| Group 3 | XX medium dosage | 1.5 mg/kg |
| Group 4 | XX low dosage | 0.75 mg/kg |

III. Test Method

The medicaments were correspondingly administered 1 ml/100 g body weight by gavage, once a day, to the animals in each test group for 14 successive days. The rat swimming test was performed one hour later after the last administration. The duration of swimming was 5 min and the length of time that the rats did not move within 5 min was recorded.

The data was given as "average±standard deviation" ($\bar{x} \pm s$). One-way analysis of variance (ANOVA) was used for data difference statistics. Differences among the groups were determined by P<0.05.

Results

The gavage administration of 1.5 mg/kg of the YY control did not shorten the length of time that the rats stopped swimming, which suggested that this dosage of YY had no antidepressive effect in the rat swimming test. 1.5 mg/kg of XX markedly shortened the length of time that the rats stopped swimming (P<0.05 v.s the blank control); 0.75 mg/kg of XX showed a tendency to shorten the length of time that the rats did not move. See Table 3 for details.

TABLE 3

Effects on Rats in the Swimming Test (n = 10, $\bar{x} \pm s$)

| Group Name | Dosage | Duration without Move within 5 min (s) |
|---|---|---|
| blank control | 10% hydroxypropyl-β-CD | 259.0 ± 21.3 |
| YY control | 1.5 mg/kg | 267.8 ± 27.0 |
| XX medium dosage | 1.5 mg/kg | 226.2 ± 43.2* |
| XX low dosage | 0.75 mg/kg | 242.4 ± 43.2 |

*$P < 0.05$, compared with blank control

Preliminary conclusions can be drawn. For example, in the three animal experimental models of acute stress depression, the positive control YY did not exhibit antidepressive effects, but it did not exclude the possibility that it would be effective in an increased dosage or in other animal models. The sample XX achieved excellent effects in all the three models, and showed relatively lower effective dosages than those of the control YY.

<Pharmacokinetic Studies>

The preferred compound of the present disclosure was assessed in rats for its pharmacokinetic profile.

Medicaments:

1-{2-[2,4-bis(trideuteriomethyl)phenylsulfanyl]phenyl}piperazine hydrobromic acid salt (XX for short)

Vortioxetine (YY for short)

Apparatuses:

Ultimate 3000 liquid chromatography system from Dionex, and

4000 Q-Trap tandem mass spectrometer equipped with electrospray ionization (ESI) source.

Animals:

SD rats, male and female, weighing 150 to 250 g

Test Conditions:

(1) HPLC

Column: Kromasil® $C_{18}$ (150×2.1 mm)

Column temperature: 25° C.

Temperature of sample injection plate: 4° C.

Sample volume: 2 μL

Mobile phase: 10 mM ammonium formate aqueous solution:methanol=15:85

Flow rate: 0.3 mL/min (2) MS Condition

The ionization source was electrospray ionization source. The detection mode was positive mode. Multiple reaction monitoring (MRM) was used as the scanning mode. The ion reaction for the quantitative analysis was the following: m/z was 305.2\150.0 for XX, and 256.1\167.1 for diphenhydramine (the internal standard).

Pharmacokinetic Test (1) Gavage Administration

XX or YY was orally administered with single dose of 20 mg/kg to six SD rats, one half of which were male and the other half was female. XX or YY was dissolved in 10% hydroxypropyl-β-cyclodextrin. Blood from the rats' orbits was collected 10 min, 30 min, 1 hr, 1.5 hr, 2 hr, 3 hr, 4 hr, 6 hr, 8 hr, 10 hr, 12 hr and 24 hr later after the administration, respectively.

(2) Intravenous Injection

Four male SD rats were taken. The dosage was calculated as 5 mL/kg body weight and 2 mg/kg. XX or YY was dissolved in DMSO (3% of a total volume) and castor oil (3% of the total volume) was added to the solution, followed by agitating with a vortex mixer. Subsequently, saline was added to the mixture to the total volume to afford the intravenous injection for the rats. The injections were intravenously administered to four male SD rats. Blood from the rats' orbits was collected 3 min, 8 min, 15 min, 30 min, 1 hr, 2 hr, 3 hr, 4 hr, 6 hr, 9 hr, 12 hr and 24 hr later after the injection, respectively.

After the blood collection, the tubes were immediately gently turned upside down at least five times to ensure sufficient mixing, and placed on ice. Heparin was added for anticoagulation. The samples were centrifuged at 8000 rpm for 5 min to separate serum from erythrocyte. The serum was transferred with a pipettor to 2 mL polypropylene (PP) tubes, which were marked with the name of the compound and the time points, and stored in a refrigerator at −40° C. before LC-MS analysis. Samples with high concentrations were diluted with rat blank plasma.

2.5 μL of Meth-H$_2$O and 5 μL of the internal standard solution (20 ng/mL, IS) were added to 50 μL of the plasma. Subsequently, 150 μL of methanol was added to the mixture to precipitate protein and the samples were then centrifuged at 13000 rpm for 5 min. The upper organic phase was taken out, filtrated with a 0.22 μM microporous membrane, and 2 μL of the sample was injected for the LC-MS analysis.

The results were listed in Tables 4 to 10.

TABLE 4

XX Concentrations in Plasma of Rats after Oral Administration of 20 mg/kg XX (ng/mL)

| Time after administration (h) | 1 | 2 | 3 | 4 | 5 | 6 | Mean ± SD |
|---|---|---|---|---|---|---|---|
| 0.16667 | 10.6 | 7 | 7.88 | 24.8 | 15.6 | 16.2 | 13.7 ± 6.65 |
| 0.5 | 45.9 | 53.2 | 41.6 | 65.2 | 88.9 | 82.7 | 62.9 ± 19.6 |
| 1 | 68.4 | 83.6 | 55.2 | 107.6 | 144 | 115.8 | 95.8 ± 32.9 |
| 1.5 | 73.4 | 91.6 | 77.4 | 120.8 | 142.8 | 109.6 | 102.6 ± 26.9 |
| 2 | 78.6 | 86.6 | 77.8 | 118.4 | 119.6 | 108 | 98.2 ± 19.5 |
| 3 | 58 | 65.8 | 53.8 | 85.8 | 77.6 | 71.2 | 68.7 ± 12.0 |
| 4 | 63.4 | 60.8 | 56 | 61.2 | 85.6 | 63.4 | 65.1 ± 10.4 |
| 6 | 46.1 | 48.7 | 36.8 | 42.8 | 54.6 | 35.5 | 44.1 ± 7.27 |
| 8 | 22.1 | 22.5 | 20.9 | 31.7 | 25.1 | 18.9 | 23.5 ± 4.49 |
| 10 | 16.7 | 17.9 | 15.5 | 20.3 | 14.9 | 13.5 | 16.5 ± 2.41 |
| 12 | 8.86 | 8.22 | 6.78 | 11.3 | 7.08 | 7.2 | 8.24 ± 1.69 |
| 14 | 4.01 | 3.56 | 7.32 | 4.43 | 3.11 | 3.19 | 4.27 ± 1.58 |
| 24 | 1.46 | 0.571 | 0.368 | 1.32 | 0.365 | 0.389 | 0.75 ± 0.51 |

TABLE 5

YY Concentrations in Plasma of Rats after Oral Administration of 20 mg/kg YY (ng/mL)

| Time after Administration (h) | 1 | 2 | 3 | 4 | 5 | 6 | Mean ± SD |
|---|---|---|---|---|---|---|---|
| 0.167 | 17.9 | 9.42 | 28.1 | 14.3 | 38.4 | 6.11 | 19.0 ± 12.2 |
| 0.5 | 86.5 | 38.1 | 52.3 | 49.7 | 57.2 | 45.8 | 54.9 ± 16.8 |
| 1 | 123 | 65.5 | 77.4 | 81.1 | 93.2 | 55.6 | 82.6 ± 23.6 |
| 1.5 | 154 | 85.2 | 82.9 | 89.2 | 73.2 | 54.9 | 89.9 ± 33.7 |
| 2 | 182 | 68.3 | 91.8 | 81.9 | 72 | 56.4 | 92.1 ± 45.7 |
| 3 | 120 | 48.2 | 58.3 | 55.9 | 42.9 | 34.2 | 59.9 ± 30.7 |
| 4 | 93.6 | 46.9 | 52.9 | 55.2 | 42.1 | 29.9 | 53.4 ± 21.6 |
| 6 | 57.4 | 37.7 | 36.7 | 33.5 | 30.5 | 22.4 | 36.4 ± 11.7 |
| 8 | 27.5 | 16.7 | 17.7 | 16.3 | 18.8 | 11.3 | 18.1 ± 5.3 |
| 10 | 14.5 | 8.39 | 10.9 | 8.32 | 9.4 | 7.24 | 9.79 ± 2.62 |
| 12 | 7.3 | 4.87 | 4.29 | 7.01 | 4.1 | 3.17 | 5.12 ± 1.67 |
| 14 | 7.19 | 2.5 | 3.69 | 4.35 | 3.79 | 2.95 | 4.08 ± 1.66 |
| 24 | 0.728 | 0.431 | 0.716 | 0.374 | 0.394 | 1.21 | 0.64 ± 0.32 |

TABLE 6

XX Concentrations in Plasma of Rats after Intravenous Injection of 2 mg/kg XX (ng/mL)

| Time after Administration (h) | 1 | 2 | 3 | 4 | Mean ± SD |
|---|---|---|---|---|---|
| 0.05 | 134.2 | 123.2 | 127.2 | 121.4 | 126.5 ± 5.68 |
| 0.133 | 86.5 | 89.0 | 85.9 | 86.8 | 87.1 ± 1.35 |
| 0.25 | 78.1 | 78.8 | 77.3 | 77.1 | 77.8 ± 0.78 |
| 0.5 | 76.6 | 76.9 | 71.3 | 75.8 | 75.2 ± 2.61 |
| 1 | 72.2 | 73.3 | 68.6 | 65.6 | 69.9 ± 3.51 |
| 2 | 60.7 | 69.5 | 68.1 | 54.4 | 63.2 ± 7.01 |
| 3 | 49.6 | 53.4 | 49.8 | 38.2 | 47.8 ± 6.60 |
| 4 | 27.2 | 38.5 | 27.6 | 25.1 | 29.6 ± 6.03 |
| 6 | 25.8 | 28.4 | 25.8 | 24.5 | 26.1 ± 1.64 |
| 9 | 14.9 | 16.1 | 18.6 | 14.1 | 15.9 ± 1.96 |
| 12 | 8.44 | 7.86 | 7.50 | 7.18 | 7.75 ± 0.54 |
| 24 | 3.38 | 2.57 | 2.89 | 3.68 | 3.13 ± 0.50 |

TABLE 7

YY Concentrations in Plasma of Rats after Intravenous Injection of 2 mg/kg XX (ng/mL)

| Time after Administration (h) | 1 | 2 | 3 | Mean ± SD |
|---|---|---|---|---|
| 0.05 | 134.2 | 123.2 | 127.2 | 213.9 ± 38.9 |
| 0.133 | 86.5 | 89 | 85.9 | 170.1 ± 7.80 |
| 0.25 | 78.1 | 78.8 | 77.3 | 136.9 ± 6.05 |
| 0.5 | 76.6 | 76.9 | 71.3 | 124.3 ± 13.0 |
| 1 | 72.2 | 73.3 | 68.6 | 94.2 ± 6.06 |
| 2 | 60.7 | 69.5 | 68.1 | 86.4 ± 16.8 |
| 3 | 49.6 | 53.4 | 49.8 | 67.0 ± 10.2 |
| 4 | 27.2 | 38.5 | 27.6 | 40.9 ± 3.40 |
| 6 | 25.8 | 28.4 | 25.8 | 33.1 ± 3.43 |
| 9 | 14.9 | 16.1 | 18.6 | 19.5 ± 1.49 |
| 12 | 8.44 | 7.86 | 7.50 | 7.85 ± 0.62 |
| 24 | 3.38 | 2.57 | 2.89 | 4.07 ± 0.05 |

TABLE 8

Pharmacokinetic Parameters of XX in Plasma of Rats after Oral Administration of 20 mg/kg XX (Mean ± SD, n = 6)

| Parameters | Units | 1 | 2 | 3 | 4 | 5 | 6 | Mean ± SD |
|---|---|---|---|---|---|---|---|---|
| $AUC_{0-t}$ | µg · h/L | 523.6 | 552.3 | 487.5 | 659.3 | 703.9 | 569.8 | 582.7 ± 82.7 |
| $AUC_{0-\infty}$ | µg · h/L | 532.2 | 552.5 | 488.9 | 666.0 | 705.3 | 571.4 | 586.0 ± 82.8 |
| $MRT_{0-\infty}$ | h | 5.62 | 4.92 | 5.44 | 5.08 | 4.24 | 4.28 | 4.93 ± 0.58 |
| $t_{1/2}$ | h | 4.0 | 1.7 | 2.8 | 3.5 | 2.6 | 2.9 | 2.92 ± 0.80 |
| Cmax | µg/L | 78.6 | 91.6 | 77.8 | 120.8 | 144 | 115.8 | 104.8 ± 26.5 |
| F % | | 11.0 | 11.5 | 10.1 | 13.8 | 14.6 | 11.9 | 12.2 ± 1.72 |

TABLE 9

Pharmacokinetic Parameters of XX in Plasma of Rats after Intravenous Injection of 2 mg/kg XX (Mean ± SD, n = 4)

| Parameter | Units | 1 | 2 | 3 | 4 | Mean ± SD |
|---|---|---|---|---|---|---|
| $AUC_{0-t}$ | µg · h/L | 462.2 | 492.9 | 466.0 | 421.5 | 460.6 ± 29.5 |
| $AUC_{0-\infty}$ | µg · h/L | 467.1 | 512.0 | 489.7 | 459.8 | 482.1 ± 23.6 |
| $MRT_{0-\infty}$ | h | 6.59 | 6.14 | 6.67 | 8.08 | 6.87 ± 0.84 |
| $t_{1/2}$ | h | 3.72 | 5.15 | 5.66 | 7.33 | 5.47 ± 1.49 |
| CL | L/h/k | 42.8 | 3.91 | 4.09 | 4.35 | 4.16 ± 0.20 |
| Vz | L/kg | 23.0 | 29.0 | 33.4 | 46.0 | 32.9 ± 9.76 |
| Cmax | µg/L | 134.2 | 123.2 | 127.2 | 121.4 | 126.5 ± 5.68 |

TABLE 10

Pharmacokinetic Parameters of YY in Plasma of Rats after Oral Administration of 20 mg/kg YY (Mean ± SD, n = 6)

| Parameters | Units | 1 | 2 | 3 | 4 | 5 | 6 | Mean ± SD |
|---|---|---|---|---|---|---|---|---|
| $AUC_{0-t}$ | µg · h/L | 836.1 | 415.8 | 480.4 | 467.8 | 427.0 | 309.2 | 489.4 ± 180.3 |
| $AUC_{0-\infty}$ | µg · h/L | 839.3 | 416.2 | 484 | 469.3 | 428.7 | 310.6 | 491.3 ± 181.0 |
| $MRT_{0-\infty}$ | h | 4.49 | 4.65 | 4.73 | 4.67 | 4.60 | 5.35 | 4.75 ± 0.31 |
| $t_{1/2}$ | h | 3.05 | 2.20 | 3.50 | 2.83 | 3.06 | 3.10 | 2.96 ± 0.43 |
| Cmax | µg/L | 182.0 | 85.2 | 91.8 | 89.2 | 93.2 | 56.4 | 99.6 ± 42.6 |
| F % | | 12.83 | 6.36 | 7.40 | 7.17 | 6.55 | 4.75 | 7.51 ± 2.77 |

TABLE 11

Pharmacokinetic Parameters of YY in Plasma of Rats after Intravenous Injection of 2 mg/kg YY (Mean ± SD, n = 3)

| Parameters | Units | 1 | 2 | 3 | Mean ± SD |
|---|---|---|---|---|---|
| $AUC_{0-t}$ | µg · h/L | 594.4 | 637.9 | 624.3 | 618.9 ± 22.2 |
| $AUC_{0-\infty}$ | µg · h/L | 627.9 | 674.6 | 660.5 | 654.4 ± 23.9 |
| $MRT_{0-\infty}$ | h | 6.56 | 6.20 | 6.50 | 6.42 ± 0.19 |
| $t_{1/2}$ | h | 5.72 | 6.15 | 6.22 | 6.03 ± 0.27 |
| CL | L/h/k | 3.19 | 2.97 | 3.03 | 3.06 ± 0.11 |
| Vz | L/kg | 26.3 | 26.3 | 27.2 | 26.6 ± 0.52 |
| Cmax | µg/L | 225.0 | 246.0 | 170.6 | 213.9 ± 38.9 |

Note:
The data of No. 4 rat was abandoned for it was abnormal.

According to the above data, $AUC_{0-t}$ of 1-{2-[2,4-bis (trideuteriomethyl) phenylsulfanyl]phenyl}piperazine hydrobromic acid salt in the rats' plasma after gavage administration of 20 mg/kg of XX was 582.7±82.7 µg·h/L, and the $AUC_{0-t}$ of Vortioxetine in the rats' plasma after gavage administration of 20 mg/kg of YY was 489.4±180.3 µg·h/L. The absolute bioavailability for rat gavage administration was 12.2±1.72%, which was calculated bis(trideuteriomethyl)phenylsulfanyl]phenyl}piperazine hydrobromic acid salt against the AUC of intravenous administration of 1-{2-[2,4-bis(trideuteriomethyl)phenylsulfanyl] phenyl}piperazine hydrobromic acid salt to rat. The AUC of Vortioxetine, with was converted based on dosage, was 7.511±2.77%. The absolute bioavailability of 1-{2-[2,4-bis (trideuteriomethyl)phenylsulfanyl]phenyl}piperazine hydrobromic acid salt is 60% higher than that of its non-deuterium counterpart; the $AUC_{0-t}$ of 1-{2-[2,4-bis(trideuteriomethyl)phenylsulfanyl]phenyl}piperazine hydrobromic acid salt was increased by 19% comparing with that of its non-deuterium counterpart.

Figure 2:
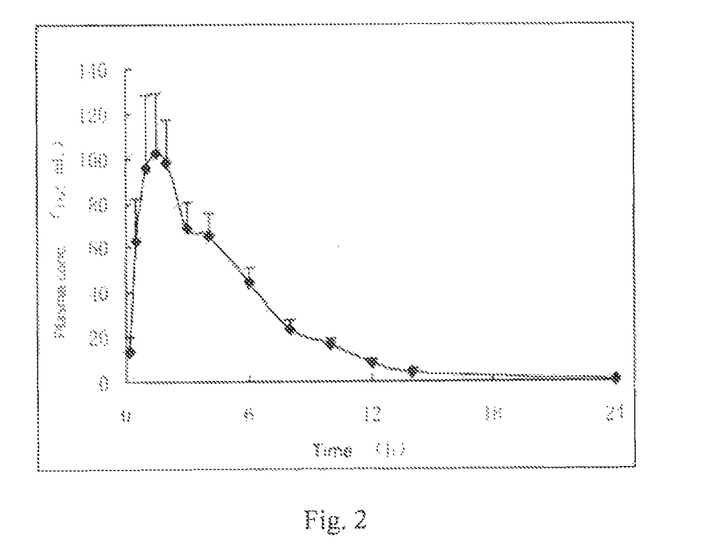
FIG. 2 is a diagram showing the average plasma concentration versus time after oral administration of 20 mg/kg 1-{2-[2,4-bis(trideuteriomethyl)phenylsulfanyl] phenyl}piperazine hydrobromide salt to rats.
Figure 3:
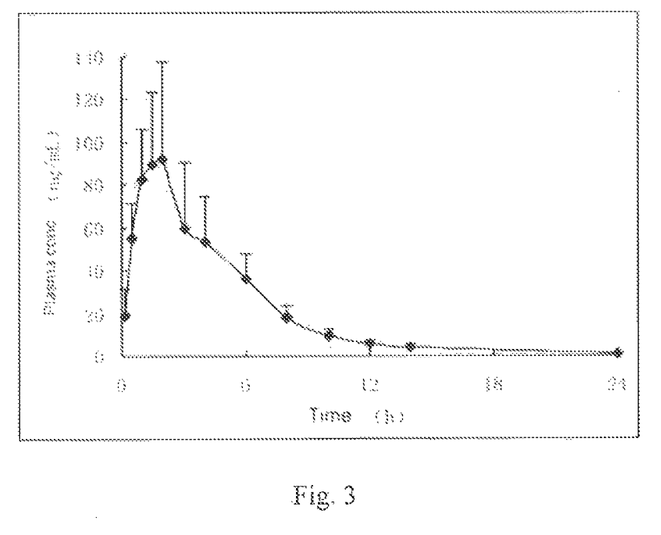
FIG. 3 is a diagram showing the average plasma concentration versus time after oral administration of 20 mg/kg of Vortioxetine to rats.

FIG. 2 is a diagram showing the average plasma concentrations versus time after oral administration of 20 mg/kg 1-{2-[2,4-bis(tridcuteriomethyl)phenylsulfanyl] phenyl}piperazine hydrobromic acid salt to rats. FIG. 3 is a diagram showing the average plasma concentrations versus time after oral administration of 20 mg/kg Vortioxetine to the rats. By comparing FIGS. 2 and 3, it can be seen that Compound (I) of the present disclosure had an improved pharmacokinetic profile and improved pharmacodynamics and therapeutic effects.

The present disclosure is presented through the above illustrative description and applications, and is not intended to be limited to the above examples. Thus, the present disclosure is not limited by those examples, and any technical solution reached through equivalent replacement is within the protection scope of the present disclosure.

What is claimed is:

1. A deuterium substituted 1-[2-(2,4-dimethyl-phenylsulfanyl)-phenyl]piperazine compound of formula (I) or a pharmaceutically acceptable salt, an N-oxide; or their stereoisomer(s), geometrical isomer(s), tautomer(s) or a mixture thereof, (I)

wherein the compound of formula (I) is selected from 1-[2-(2-methyl-4-trideuteriomethyl-phenylsulfanyl) phenyl]piperazine, 1-{2- [2,4-bis(trideuteriomethyl) phenylsulfanyl]phenyl }piperazine, 1-[2-(2-methyl-4-dideuteriomethyl-phenylsulfanyl) phenyl]piperazine, 1-{2-[2,4-bis(monodeuteriomethyl) phenylsulfanyl] phenyl }piperazine, 1-[2-(2-monodeuteriomethyl-4-trideuteriomethyl-phenylsulfanyl) phenyl]piperazine, 1-[2-(2-methyl-4-trideuteriomethyl-phenylsulfanyl) phenyl]octodeuteriopiperazine and 1-{2-[2,4-bis(trideuteriomethyl) phenylsulfanyl] phenyl}octodeuteriopiperazine.

2. The compound according to claim 1, wherein the pharmaceutically acceptable salt is an addition salt of the compound of formula (I) with hydrobromic acid.

3. A pharmaceutical composition, comprising: the compound according to claim 1; and one of a pharmaceutically acceptable carrier, excipient, diluent, adjuvant and medium, or a combination thereof.

4. A method of treating a disease, comprising administering the compound of claim 1 to a person in need thereof, wherein the disease is selected from depression, flush, affective disturbance, sleep apnea, anxiety, attention deficit hyperactivity disorder (ADHD), post-traumatic stress disorder (PTSD), irritable bowel syndrome (IBS), alcoholism, drug addiction and drug abuse.

5. A pharmaceutical composition, comprising: the compound according to claim 2; and one of a pharmaceutically acceptable carrier, excipient, diluent, adjuvant and medium, or a combination thereof.

6. A method of treating a disease, comprising administering the compound of claim 2 to a person in need thereof, wherein the disease is selected from depression, flush, affective disturbance, sleep apnea, anxiety, attention deficit hyperactivity disorder (ADHD), post-traumatic stress disorder (PTSD), irritable bowel syndrome (IBS), alcoholism, drug addiction and drug abuse.

* * * * *